United States Patent
Chen et al.

(10) Patent No.: US 6,953,551 B2
(45) Date of Patent: Oct. 11, 2005

(54) MICROARRAY FABRICATION TECHNIQUES AND APPARATUS

(75) Inventors: Shiping Chen, Rockville, MD (US); Yuling Luo, Castro Valley, CA (US)

(73) Assignee: Genospectra, Inc., Fremont, CA (US)

(*) Notice: Subject to any disclaimer, the term of this patent is extended or adjusted under 35 U.S.C. 154(b) by 597 days.

(21) Appl. No.: 09/791,998

(22) Filed: Feb. 22, 2001

(65) Prior Publication Data

US 2001/0053334 A1 Dec. 20, 2001

Related U.S. Application Data

(60) Provisional application No. 60/244,413, filed on Oct. 30, 2000, provisional application No. 60/220,085, filed on Jul. 21, 2000, provisional application No. 60/216,265, filed on Jul. 6, 2000, provisional application No. 60/188,872, filed on Mar. 13, 2000, and provisional application No. 60/183,737, filed on Feb. 22, 2000.

(51) Int. Cl.[7] .............................. B01L 3/02; B41K 1/38
(52) U.S. Cl. .................. 422/100; 73/864.01; 73/863.31; 222/145.3; 101/327; 101/335; 101/368.7
(58) Field of Search ............... 422/100, 99; 73/864.01, 73/863.31, 863.81, 864.31; 222/145.3; 101/335, 327, 368, 93.37, 97, 98, 333; 400/124.1

(56) References Cited

U.S. PATENT DOCUMENTS

| | | | |
|---|---|---|---|
| 4,010,019 A | | 3/1977 | Cole et al. |
| 4,621,665 A | * | 11/1986 | Webb ........................ 141/1 |
| 4,877,745 A | | 10/1989 | Hayes et al. |
| 4,964,539 A | * | 10/1990 | Mueller .................... 222/94 |
| 4,981,783 A | | 1/1991 | Augenlicht |
| 5,102,016 A | * | 4/1992 | Ball et al. ................ 222/145.3 |
| 5,143,854 A | | 9/1992 | Pirrung et al. |
| 5,265,327 A | | 11/1993 | Faris et al. |
| 5,276,327 A | | 1/1994 | Bossen et al. |
| 5,384,261 A | | 1/1995 | Winkler et al. |

(Continued)

FOREIGN PATENT DOCUMENTS

| | | |
|---|---|---|
| EP | 0 955 084 A1 | 11/1999 |
| EP | 1 157 737 | 11/2001 |
| JP | 07-023995 | 1/1995 |

(Continued)

OTHER PUBLICATIONS

U.S. Appl. No. 10/431,169, filed May 6, 2003, Chen et al.
Eisen, M.B. and Brown, P.O. (1999). "12 DNA Arrays For Analysis of Gene Expression," *Method In Enzymology,* 303:179–205.
Lashkari, D. A. et al. (1997). "Yeast Microarrays for Genome Wide Parallel Genetic and Gene Expression Analysis," *Proc. Natl. Acad. Sci. USA Genetics* 94:13057–13062.
Lemieux, B. et al. (1998). "Overview of DNA Chip Technology," *Molecular Breeding,* 4:277–289.

(Continued)

*Primary Examiner*—Jill Warden
*Assistant Examiner*—Brian R. Gordon
(74) *Attorney, Agent, or Firm*—Morrison & Foerster LLP (57) ABSTRACT

Disclosed is a microarray printing system and methods of printing probe microarrays. The system has a print-head formed of one or more capillary bundle, such as light-guiding capillaries. The bundles may especially be bundles of capillaries that provide a large number of probes on the surface of a substrate. Methods of registering or correlating the distal and proximal ends of the capillaries are also provided. Further, the invention provides methods and equipment for identifying defective microarrays that are missing one or more probes from the surface of the microarray.

23 Claims, 4 Drawing Sheets

U.S. PATENT DOCUMENTS

| | | | |
|---|---|---|---|
| 5,436,327 | A | 7/1995 | Southern et al. |
| 5,445,934 | A | 8/1995 | Fodor et al. |
| 5,474,796 | A | 12/1995 | Brennan |
| 5,525,464 | A | 6/1996 | Drmanac et al. |
| 5,565,324 | A | 10/1996 | Still et al. |
| 5,593,839 | A | 1/1997 | Hubbell et al. |
| 5,604,587 | A | 2/1997 | Che et al. |
| 5,615,803 | A * | 4/1997 | Hatakeyama et al. ......... 222/94 |
| 5,630,925 | A | 5/1997 | Pentoney, Jr. et al. |
| 5,658,802 | A | 8/1997 | Hayes et al. |
| 5,690,894 | A | 11/1997 | Pinkel et al. |
| 5,700,637 | A | 12/1997 | Southern |
| 5,702,033 | A * | 12/1997 | Beaver ......................... 222/94 |
| 5,740,297 | A | 4/1998 | Onishi et al. |
| 5,741,554 | A | 4/1998 | Tisone |
| 5,744,305 | A | 4/1998 | Fodor et al. |
| 5,770,151 | A | 6/1998 | Roach et al. |
| 5,770,367 | A | 6/1998 | Southern et al. |
| 5,770,722 | A | 6/1998 | Lockhart et al. |
| 5,800,992 | A | 9/1998 | Fodor et al. |
| 5,807,522 | A | 9/1998 | Brown et al. |
| 5,831,070 | A | 11/1998 | Pease et al. |
| 5,837,832 | A | 11/1998 | Chee et al. |
| 5,900,481 | A | 5/1999 | Lough et al. |
| 5,919,523 | A | 7/1999 | Sundberg et al. |
| 5,948,624 | A | 9/1999 | Rothschild et al. |
| 6,027,873 | A | 2/2000 | Schellenberger et al. |
| 6,048,695 | A | 4/2000 | Bradley et al. |
| 6,054,270 | A | 4/2000 | Southern |
| 6,083,763 | A | 7/2000 | Balch |
| 6,101,946 | A | 8/2000 | Martinsky et al. |
| 6,110,426 | A | 8/2000 | Shalon et al. |
| 6,129,243 | A * | 10/2000 | Pal et al. ....................... 222/94 |
| 6,136,962 | A | 10/2000 | Shi et al. |
| 6,176,395 | B1 * | 1/2001 | Abbott et al. ................. 222/94 |
| 6,235,473 | B1 | 5/2001 | Friedman et al. |
| 6,270,340 | B1 | 8/2001 | Lepp |
| 6,308,862 | B1 * | 10/2001 | Fillmore et al. .............. 222/94 |
| 6,312,970 | B1 | 11/2001 | Ogawa |
| 6,350,618 | B1 * | 2/2002 | Borrelli et al. ............. 436/174 |
| 6,387,331 | B1 | 5/2002 | Hunter |
| 6,596,237 | B1 * | 7/2003 | Borrelli et al. ............. 422/100 |
| 2002/0028160 | A1 * | 3/2002 | Xiao et al. ................... 422/100 |
| 2002/0072111 | A1 | 6/2002 | Clarkin et al. |
| 2002/0164824 | A1 * | 11/2002 | Xiao et al. ................... 436/524 |
| 2003/0124734 | A1 * | 7/2003 | Dannoux .................... 436/180 |
| 2003/0143725 | A1 | 7/2003 | Chen et al. |

FOREIGN PATENT DOCUMENTS

| | | |
|---|---|---|
| JP | 2000-245460 | 9/2000 |
| JP | 2000-245461 | 9/2000 |
| JP | 2000-270877 | 10/2000 |
| JP | 2000-270878 | 10/2000 |
| JP | 2000-270879 | 10/2000 |
| JP | 2000-279177 | 10/2000 |
| JP | 2000-342298 | 12/2000 |
| WO | WO 97/18226 A1 | 5/1997 |
| WO | WO 98/29736 A1 | 7/1998 |
| WO | WO 98/55593 | 12/1998 |
| WO | WO 99/13312 | 3/1999 |
| WO | WO 99/34920 | 7/1999 |
| WO | WO 99/40434 | 8/1999 |
| WO | WO 99/55460 A1 | 11/1999 |
| WO | WO 99/55461 A1 | 11/1999 |
| WO | WO 00/01798 | 1/2000 |
| WO | WO 00/01859 A3 | 1/2000 |
| WO | WO 00/13796 A1 | 3/2000 |
| WO | WO 00/43752 A1 | 7/2000 |
| WO | WO 00/50871 A1 | 8/2000 |
| WO | WO 00/53736 A1 | 9/2000 |
| WO | WO 00/53739 A1 | 9/2000 |
| WO | WO 00/62934 A1 | 10/2000 |
| WO | WO 00/66360 A1 | 11/2000 |
| WO | WO 00/76662 A2 | 12/2000 |
| WO | WO 01/06011 A2 | 1/2001 |
| WO | WO 01/30498 A1 | 5/2001 |
| WO | WO 01/31317 A1 | 5/2001 |
| WO | WO 01/31333 A1 | 5/2001 |

OTHER PUBLICATIONS

Rogers, Y–H et al. (1999). "Immobilization of Oligonucleotides Onto A Glass Support Via Disulfide Bonds: A Method For Preparation of DNA Microarrays," *Analytical Biochemistry,* 266(1):23–30.

Schena, M. (1996). "Genome Analysis with Gene Expression Microarrays," *BioEssays* 18(5):427–431.

Yu–Hui R. et al. (1999). "Immobilization of Oligonucleotides Onto A Glass Support Via Disulfide Bonds:A Method For Preparation of DNA Microarrays," *Analytical Biochemistry,* 266(1):23–30.

Schena, M. et al. (Jul. 1998). "Microarrays: Biotechnology's Discovery Platform for Functional Genomics," *TIBTECH* 16(7):301–306.

Shalon et al. (1996). "A DNA Microarray System for Analyzing Complex DNA Samples Using Two–Color Fluorescent Probe Hybridization," *Genome Res* 6:639–645.

Zhou et al. (2001). "Solution and Chip Arrays in Protein Profiling," *Trends Biotechnol* 10(Suppl):S34–39.

Ayadim, M. et al. (1995). "Photosensitizers Covalently Anchored to the Silica Surface: Modulation of the Excited State Efficiency through Electron Transfer from the Linking Arm or from the Surface," *Tetrahedron Letts.* 36:4615–4618.

Beier, M. et al. (May 1, 1999). "Versatile Derivatisation of Solid Support Media for Covalent Bonding on DNA–Microchips," *Nucl. Acids Res.* 27(9):1970–1977.

Brown et al. (Sep. 1995). "A Single–Bead Decode Strategy Using Electrospray Ionization Mass Spectrometry and a New Photolabile Linker: 3–Amino–3–(2–Nitrophenyl)Propionic Acid," *Molecular Diversity* 1(1):4–12.

Camilleri, P., ed. (1998). *Capillary Electrophoresis: Theory and Practice.* CRC Press; New York, NY., 2 pages total (Table of Contents only).

Dorman, G. et al. (Feb. 2000). "Using Photolabile Ligands in Drug Discovery and Development," *Trends Biotechnol.* 18:64–77.

Hermanson, G.T. (1995). *Bioconjugate Techniques.* Academic Press, pp. ix–xx (Table of Contents only).

Olejnik, J. et al. (Oct. 1996). "Photocleavable Biotin Phosphoramidite for 5'–End–Labeling, Affinity Purification and Phosphorylation of Synthetic Oligonucleotides," *Nucl. Acids Res.* 24(2):361–366.

Pinkel, D. et al. (Oct. 1998). "High Resolution Analysis of DNA Copy Number Variation Using Comparative Genomic Hybridization to Microarrays," *Nat. Genet.* 20:207–211.

Rogers, Y.H. et al. (Jan. 1, 1999). "Immobilization of Oligonucleotides onto a Glass Support via Disulfide Bonds: A Method for Preparation of DNA Microarrays," *Anal. Biochem.* 266(1):23–30.

Sano, T. et al. (Dec. 1991). "A Streptavidin–Protein A Chimera that Allows One–Step Production of a Variety of Specific Antibody Conjugates," *Bio/Technol.* 9:1378–1381.

Schena, M. et al. (Oct. 20, 1995). "Quantitative Monitoring of Gene Expression Patterns with a Complementary DNA Microarray," *Science* 270:467–470.

Wilcheck, M. et al. (1990). "Applications of Avidin–Biotin Technology: Literature Survey," *Meth. Enzymol.* 184:14–45, 529–537, 588–600.

Wong, S.S. (1991). *Chemistry of Protein Conjugation and Cross Linking.* CRC Press; Boston, MA., 7 pages total (Table of Contents only).

* cited by examiner

MICROARRAY FABRICATION TECHNIQUES AND APPARATUS

This invention claims the benefit of priority to U.S. Provisional Application Nos.: 60/183,737, filed on Feb. 22, 2000; 60/188,872, filed on Mar. 13, 2000; 60/216,265, filed on Jul. 6, 2000; 60/220,085, filed on Jul. 21, 2000; 60/244,413, filed on Oct. 30, 2000. This invention is also related to PCT/US01/05844, titled MICROARRAY FABRICATION TECHNIQUES AND APPARATUS by inventors Shiping Chen, Yuling Luo, and Anthony C. Chen, filed on even date herewith. All of the above applications are incorporated by reference herein in their entireties as if fully set forth below.

FIELD OF THE INVENTION

The invention relates to mechanisms and methods used to form a microarray of multiple probes used to detect the presence of a target biological material or a target chemical.

BACKGROUND

A microarray is an array of spots of biological or chemical samples ("probes") immobilized at predefined positions on a substrate. Each spot contains a number of molecules of a single biological or chemical material. To interrogate the array, the microarray is flooded with a fluid containing one or more biological or chemical samples (the "target"), elements of which typically interact with one or more complementary probes on the microarray. In DNA microarrays in particular, the probes are oligonucleotide or cDNA strains, and the target is a fluorescent or radioactive-labeled DNA sample. The molecular strands in the target hybridize with complementary strands in the probe microarray. The hybridized microarray is inspected by a microarray reader, which detects the presence of the radioactive labels or which stimulates the fluorescent labels to emit light through excitation with a laser or other energy sources. The reader detects the position and strength of the label emission in the microarray. Since the probes are placed in predetermined and thus known positions in the microarray, the presence and quantity of target sequences in the fluid are identified by the position at which fluorescence or radiation is detected and the strength of the fluorescence or radiation.

Microarray technology provides an extremely useful tool to conduct biological or chemical experiments in a massive parallel fashion because of the large number of different probes that one can fabricate onto the microarray. It is particularly powerful in screening, profiling and identifying DNA samples.

Microarrays today come as two-dimensional probe matrices fabricated on solid glass or nylon substrates. Because the target samples are generally hard to produce or very expensive, it is highly desirable to perform assays on as many features as possible on a single microarray. This calls for a significant increase in probe density and quantity on a single substrate. In general, microarrays with probe pitch smaller than 500 $\mu$m (i.e. density larger than 400 probes per sqr. centimeter) is referred as high density microarrays, otherwise, they are "low density" microarrays.

There are two microarray fabrication techniques on the market, photolithographic and robotic spotting techniques. The photolithographic technique [U.S. Pat. Nos. 5,445,934, 5,744,305] adapts the same fabrication process for electronic integrated circuits to synthesize probes in situ base by base. This technique requires a large capital outlay for equipment running up to hundreds of millions of dollars. The initial setup of new microarray designs is also very expensive due to the high cost of producing photo masks. This technique is therefore only viable in mass production of standard microarrays at a very high volume. Even at high volumes, the complexity in synthesis still limits the production throughput resulting in a high microarray cost. This complexity also limits the length of the synthesized DNA strain to the level of a short oligonucleotide (~25 bases), which reduces the specificity and sensitivity of hybridization in some applications.

The established robotic spotting technique [U.S. Pat. No. 5,807,522] uses a specially designed mechanical robot, which produces a probe spot on the microarray by dipping a pin head into a fluid containing an off-line synthesized DNA and then spotting it onto the slide at a predetermined position. Washing and drying of the pins are required prior to the spotting of a different probe in the microarray. In current designs of such robotic systems, the spotting pin, and/or the stage carrying the microarray substrates move along the XYZ axes in coordination to deposit samples at controlled positions of the substrates. Because a microarray contains a very large number of different probes, this technique, although highly flexible, is inherently very slow. Even though the speed can be enhanced by employing multiple pin-heads and spotting multiple slides before washing, production throughput remains very low. This technique is therefore not suitable for high volume mass production of microarrays.

In addition to the established quill-pin spotting technologies, there are a number of microarray fabrication techniques that are being developed. These include the inkjet technology and capillary spotting.

Inkjet technology is being deployed to deposit either cDNA/oligonucleotides, or individual nucleotides at defined positions on a substrate to produce an oligonucleotide microarray through in situ synthesis. Consequently, an oligonucleotide is produced in situ one base at a time by delivering monomer-containing solutions onto selected locations, reacting the monomer, rinsing the substrate to remove excess monomers, and drying the substrate to prepare it for the next spot of monomer reactant.

An emerging spotting technique uses capillaries instead of pins to spot DNA probes onto the support. Four references discuss capillary-based spotting techniques for array fabrication:

WO 98/29736, "Multiplexed molecular analysis apparatus and method", by Genometrix Inc.

WO 00/01859, "Gene pen devices for array printing", by Orchid Biocomputer Inc.

WO 00/13796, "Capillary printing system", by Incyte Pharmaceuticals Inc.

WO 99/55461, "Redrawn capillary imaging reservoir", by Corning Inc.

In summary, due to the high cost of production, microarrays fabricated with existing technologies are far too expensive as a single use lab supply.

SUMMARY OF THE INVENTION

This invention provides a capillary bundle for delivering probe microarrays on a substrate, the capillary bundle comprises a body having a proximal end for supplying probes and a distal end for delivering probes to the microarray, a plurality of isolated channels for transporting the probes between the ends, each of said channels extending from the proximal end to the distal end and being surrounded by a channel wall; at least an elongated portion of the body is located between the distal end and the proximal end and is flexible such that the distal end may move independently of the proximal end; and where at least at the proximal and distal ends a cross-section of said capillary bundle as defined by any section orthogonal to a length of said capillary bundle comprises a continuous structure.

Another variation of the invention includes a capillary bundle comprising a body having a proximal end and a distal end; a plurality of isolated channels, each channel extending from the proximal end to the distal end and being surrounded by a channel wall, at least one of the channels having an individual well where the channel exits the capillary bundle from the distal end; and where at least at the proximal and the distal ends a cross-section of the capillary bundle as defined by any section orthogonal to a length of the capillary bundle comprises a continuous structure.

Another variation of a capillary bundle comprises a body having a proximal end and a distal end; a plurality of isolated channels, each of the channels extending from the proximal end to the distal end and being surrounded by a channel wall having a first region in communication with the channel and at least a second region on a side of the first region opposite to the channel, where the first region has an optical refractive index higher than an optical refractive index of the second region so that light transmitted into the proximal end of the channel exits the capillary bundle at the distal end of the channel; and where at least at the proximal and the distal ends, a cross-section of the capillary bundle as defined by any section orthogonal to a length of the capillary bundle comprises a continuous structure. The first region of the channel wall may be doped with Germanium or lead.

Another variation of the invention may include at least an elongated portion of the body located between the distal end and the proximal end which is flexible such that the distal end may move independently of the proximal end.

In another variation, the capillary bundle may include at least one of the plurality of channels having an individual well located on the distal end where the channel exits from the distal end.

The capillary bundle of the present invention may also comprise a continuous cross section throughout an entirety of the capillary bundle.

The capillary bundle of the present invention may comprise silica or a polymer.

In another variation, the capillary bundle of the present invention may include a portion of the channel wall at the distal end which is coated with an electrically-conductive material. Also, at least a portion of the channel wall at the proximal end may be coated with an electrically-conductive material.

Another variation of the capillary bundle of the present invention may include at least a portion of the channel wall being coated with a hydrophobic film.

Another variation of the capillary bundle of the present invention includes, the plurality of channels forming a first arrangement at the proximal end, and a second arrangement at the distal end, and the first arrangement being identical to the second arrangement. By arrangement is meant the position or location of a channel opening relative to the remaining channels in the bundle.

In the capillary bundle of the present invention, a cross-sectional area of each of the channels in the first arrangement may be greater than a cross-sectional area of each of the channels in the second arrangement.

The capillary bundle of the present invention is of such a density that it may contain from 1000 to more than 500,000 channels that print non-overlapping spots in an area of no more than 12 $cm^2$ on a substrate.

The invention further includes a print-head for printing probe microarrays on a substrate, wherein the print-head comprises at least one capillary bundle of the invention described herein. Alternatively, the print-head may comprise a plurality of capillary bundles of the invention described herein. The present invention may also include a print head as described herein where the proximal end of each capillary bundle is separated from another proximal end of another capillary bundle. Such a configuration may improve the efficiency and space when providing probe material to the proximal ends of the bundles while the distal ends of the bundles may be grouped together in a print head. The invention further includes a frame that is adapted to hold each of the distal ends of each capillary bundle in a print head.

The invention includes a print system for printing probe microarrays comprising a print-head as described herein, a plurality of reservoirs in fluid communication with the proximal ends of the channels of the capillary bundles, a voltage source connected to the electrically-conductive material at the proximal end and the electrically conductive material at the distal end of each of the channels, and a voltage controller being configured to individually adjust and control the voltage applied to each of the channels.

The print system of the present invention may comprise a print-head according to the invention described herein and a plurality of reservoirs in fluid communication with the channels at the distal ends of the capillary bundle. A variation of the print system may include a plurality of reservoirs comprising a microtitre plate having wells. In another variation of the print system, the channels at the distal end may have an increased cross sectional area such that the distal end channels serve as reservoirs.

The print system according the invention describe herein may further comprise a flexible mount on which a substrate is placed prior to printing, the flexible mount being configured to move so that the capillary bundle for printing probe arrays contacts the substrate across the distal end of the capillary bundle despite the print-head and the substrate being aligned so that the print-head would not contact the substrate across the distal end of the capillary bundle in the absence of the flexible mount. A variation of the print system may comprise reservoirs residing in fixed positions, and wherein the capillary bundle for printing probe arrays is movable in relation to the reservoirs.

The invention further includes a method of making a capillary bundle suitable for printing a probe microarray on a substrate.

The method may comprise forming a plurality of capillary preforms into an continuous and orderly matrix having substantially coplanar first and second ends where each the capillary has a body and a channel defined by a wall, the channel extending from the first end to the second end, joining at least the proximal and distal ends of the capillary preforms to form a continuous structure, extending the continuous structure to increase a distance between the first and second ends, where a cross-sectional area of each of the channels between the first and second ends decreases while remaining proportional to a cross-sectional area of each of the channels at the first and second ends, separating the capillary bundle between the first and second ends to form at least one capillary bundle wherein the first and second ends each define a proximal end of the capillary bundle and the separated ends each define a distal end of the capillary bundle.

A variation of the inventive method includes forming at least one well on at least one of the capillary bundles where the channel exits the capillary bundle at the distal end.

Another variation of the inventive method include forming a flexible portion of the capillary bundle between the proximal and distal ends during the extending step such that the distal end may be moved independent of the proximal end.

Another variation of the inventive method includes making a capillary bundle suitable for printing a probe microarray on a substrate, comprising forming a plurality of capillary preforms into a continuous and orderly matrix having substantially coplanar first and second ends where each the capillary has a body and a channel defined by a wall, the channel extending from the end to the second end, where the wall has a higher optical refractive index than an optical refractive index of a remainder of a body of the capillary; and joining at least the first and second ends of the capillaries to form a continuous bundle.

The invention also includes the methods described herein further comprising extending the capillary bundle to increase a distance between the first and second ends, where a cross-sectional area of each of the channels between the first and second ends decreases while remaining proportional to a cross-sectional area of each of the channels at the first and second ends, and separating the capillary bundle between the first and second ends to form two capillary bundles wherein the first and second ends define a proximal end of each of the capillary bundles and the separated ends of capillary bundle form distal ends of each of the capillary bundles.

A variation of the methods of the present invention include wherein at least one capillary of the plurality of capillaries comprises silica and wherein at least the wall of the channel at the distal end of the capillary has been doped with an etch-rate increasing chemical, and wherein the method further comprises etching the distal end of the capillary to form a well within the channel wall at the distal end of the capillary.

A variation of the methods of the present invention further comprise the step of forming at least one well by drilling into the channel wall at the distal end of the capillary.

The methods of the present invention may include a securing step which comprises heating the plurality of capillaries to form the continuous structure.

The methods of the present invention may also include a forming step which comprises selecting the plurality of capillaries wherein the wall is doped with Germamium.

Another variation of the invention includes a method of making a microarray comprising depositing a probe on a substrate using a capillary bundle, a print head and/or a print system as described herein.

Another variation of the invention includes a method of printing an array of probes providing a print-head having a printing surface and having a plurality of probe transporting channels exiting from the printing surface, at least one channel having a well on the printing surface, providing a substrate having a surface and placing the substrate in a mount, contacting the print-head surface and the substrate, and depositing the probes on the substrate within the wells of the printing surface to limit the spread of the probes across the substrate.

Another variation of the invention includes a method of printing an array of probes providing a print-head having a printing surface and having a plurality of light transmitting and probe transporting channels exiting from the printing surface, providing a substrate comprising a light sensitive, hydrophobic surface which become hydrophilic after exposure to light and placing the substrate in a mount, transmitting light through the channels to expose discrete areas on the substrate surface to light, and depositing the probes on the hydrophilic array on the substrate surface.

The methods described herein may include transmitting light through the channels to expose discrete areas on the substrate surface to light forms a hydrophilic array on the substrate surface The methods described herein may include providing the channels with wells on the printing surface, and may further comprise the step of contacting the printing surface with the substrate, wherein exposure of the substrate surface to the transmitted light is limited to the substrate surface within each the well.

The methods described herein may include configuring at least one of the print-head and the mount to move so that the printing surface of the print-head and the substrate surface are parallel when depositing the probes despite the print-head and the substrate being previously aligned so that the print-head surface would not be parallel to the substrate surface. The method may include configuring the mount to pivot. Alternatively, the print-head may be formed of a material that is sufficiently elastic that the print-head flexes when the print-head contacts the substrate.

The invention further includes increasing a viscosity of the probes to reduce overlapping of probes or reducing the time during which the probe is deposited on the substrate. In another variation, the invention includes heating the substrate in a dry environment to accelerate evaporation of fluids in the probe. Yet another variation includes reducing a surface temperature of the substrate below a freezing point of the probe fluid.

Another variation of the invention includes the method of printing an array of probes as described herein where the depositing step comprises electrically depositing the probes by applying a voltage between the substrate and the print-head.

Yet another variation of the invention includes the method of printing an array of probes as described herein wherein the probes are in the form selected from the group consisting of a bead, gel, and paste.

The invention thus provides a number of systems, components, means, and methods for producing probe arrays as are more fully described below. This Summary section of the disclosure provides a summary of some salient points of the invention, but this section is not to be interpreted as limiting the scope of the invention to only those features and embodiments discussed in this section. Instead, the invention involves all components, systems, and methods discussed in this and the following sections in addition to those defined by the appended claims.

The invention further includes a microarray comprising a substrate coated with a layer of light sensitive material, and a plurality of discrete probes arranged in a matrix on said substrate. A variation of the invention includes a microarray in which the light sensitive material may be hydrophobic and may become hydrophilic after exposure to light. The probes of a microarray of the present invention may be located on a portion of the substrate that is hydrophilic.

Another variation of the invention includes a microarray formed from a print-head having a plurality of channels having wells, the microarray comprising a substrate, a plurality of discrete probes arranged in a matrix on the substrate by each of the channels, wherein each individual probe covers an area on the substrate that is less than or equal to an area of the respective well of the channel.

Another variation of the invention may include a microarray formed from a print-head having a plurality of channels having wells, the microarray comprising a substrate, a plurality of discrete probes arranged in a matrix on the substrate wherein the probe is deposited on a carrier on the substrate.

The microarray of the present invention may include a carrier which comprises a bead, gel, or paste. The present invention also includes a microarray wherein the matrix comprises at least 1,000 to 500,000 or more discrete probes in an area of no more than 12 cm$^2$.

The microarray of the present invention may include a probe material which is selected from a group consisting of biological or chemical materials. The biological or chemical materials may be selected from a group consisting of deoxyribonucleic acids (DNA), ribonucleic acids (RNA), sythetic oligonucleotides, antibodies, proteins, peptides, lectins, modified polysaccharides, synthetic composite macromolecules, functionalized nanostructures, synthetic polymers, modified/blocked nucleotides/nucleosides, modified/blocked amino acides, fluorophores, chromophores, ligands, chelates, haptens and drug compounds.

PREFERRED EMBODIMENT AND FURTHER DISCUSSION OF THE INVENTION

In the description below, a DNA microarray is used as one embodiment of the invention. The techniques described herein can also be used to produce microarrays of a wide range of biological and chemical materials. For example A "probe," as used herein, is a set of copies of one type of molecule or one type of multimolecular structure which is capable of specific binding to a particular sample or portion of a sample. "Probes," as used herein, refers to more than one such set of molecules. A probe may be immobilized on the substrate by either covalent or noncovalent attachment. Probes may be polynucleotides, polypeptides, oligosaccharides, polysaccharides, antibodies, cell receptors, ligands, lipids, cells, or combinations of these structures, or any other structures to which samples of interest or portions of samples of interest will bind with specificity. The set of probes chosen depends on the use of the apparatus. For example, if the apparatus uses polynucleotides as probes, if one is performing sequence analysis, one would prefer a complete or nearly complete set of n-mers; the use of such sets is more fully described in U.S. Pat. Nos. 5,700,637 and 6,054,270, which are hereby incorporated herein by reference in their entirety. On the other hand, if a device is to be used to analyze mutations or polymorphisms in a gene or set of genes, polynucleotides representing a complete or chosen set of mutations, such as substitution, deletion, and insertion mutations, for sections of the particular gene or genes of interest may be preferred. As a further example, in diagnostics such as for cancer-related mutations, particular mutational "hot spots" in a set of genes known to be associated with a particular cancer or cancers would be the areas to which complementary polynucleotides would serve as the set of probes. These examples are merely illustrative of the various custom sets of probes that might be selected for a particular apparatus and focus on polynucleotides because these are the types of probes now most commonly in use; it is to be understood that other types of probes and other sets of polynucleotides will be readily apparent to the skilled worker in the field.

As used herein, "polynucleotide" means a polymeric form of nucleotides of any length, which contain deoxyribonucleotides, ribonucleotides, and/or their analogs. The terms "polynucleotide" and "nucleotide" as used herein are used interchangeably. Polynucleotides may have any three-dimensional structure, and may perform any function, known or unknown. The term "polynucleotide" includes double- or single-stranded, and triple-helical molecules. Unless otherwise specified or required, any embodiment of the invention described herein that includes a polynucleotide encompasses both the double-stranded form and each of two complementary single-stranded forms known or predicted to make up the double stranded form. Relatively shorter lengths of polynucleotides (less than about 100 nucleotides) are also referred to as oligonucleotides.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. Analogs of purines and pyrimidines are known in the art, and include, but are not limited to, aziridinylcytosine, 4-acetylcytosine, 5-fluorouracil, 5-bromouracil, 5-carboxymethylaminomethyl-2-thiouracil, 5-carboxymethylaminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, pseudoruacil, 5-pentynyluracil and 2,6-diaminopurine. The use of uracil as a substitute for thymine in a deoxyribonucleic acid is also considered an analogous form of pyrimidine.

If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications included in this definition are, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s).

Further, any of the hydroxyl groups ordinarily present in the sugars may be replaced by phosphonate groups, phosphate groups, protected by standard protecting groups, or activated to prepare additional linkages to additional nucleotides or to solid supports. The 5' and 3' terminal OH groups can be phosphorylated or substituted with amines or organic capping groups moieties of from 1 to 20 carbon atoms. Other hydroxyls may also be derivatized to standard protecting groups.

Polynucleotides can also contain analogous forms of ribose or deoxyribose sugars that are generally known in the art, including, but not limited to, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1–20 C) optionally containing and ether (—O—) linkage, aryl, alkenyl, cycloalky, cycloalkenyl or araldyl. Not all linkages in a polynucleotide need be identical. Substitution of analogous forms of sugars, purines and pyrimidines can be advantageous in designing a final product, as can alternative backbone structures like a polyamide backbone.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains.

A "ligand," as used herein, is a molecule which binds to a particular receptor. The receptor may be a cell receptor or it may be a portion of another molecule, for example, a receptor for an allosteric modifier of an enzyme. Examples of ligands include, but are not limited to, enzyme cofactors, substrates and inhibitors, allosteric modifiers of enzymes, agonists and antagonists for cell membrane receptors, toxins and venoms, viral epitopes, haptens, hormones, lectins, and drugs such as opiates and steroids.

A "cell receptor," as used herein, is a cellular molecule, which may be normally located either intracellularly or in association with the cell membrane, which has an affinity for a given ligand. Examples include, but are not limited to, hormone receptors, cellular transporters, cytokine receptors, and neurotransmitter receptors.

The samples being deposited on the microarray substrate using the technology disclosed herein can take or be carried by any physical form that can be transported through a capillary. These include but not limited to fluid, gel, paste, bead, powder and particles suspended in liquid.

The substrate of the invention can be made of various materials. The substrate is required to be capable of immobilizing the particular probes used, or the substrate must be capable of modification (for example, by coating) so that it is capable of such immobilization. Preferred materials for the substrate of the present invention include silica, glass, metals, plastics, and polymers.

For immobilizing polynucleotides and polypeptides, silica, i.e. pure glass, is a preferred material because polynucleotides and polypeptides can be covalently attached to a treated glass surface and silica gives out a minimum fluorescent noise signal. The silica may be layered on another material, or it may be core or base material of the apparatus, or both. Another example of a substrate includes a plastic or polymer tape as a base substrate, with a coating of silica for probe embodiment. In this embodiment, a further layer of metallic material may be added, either on the opposite side of the tape from the silica layer, or sandwiched between the silica layer and the polymer or plastic.

Figure 1:
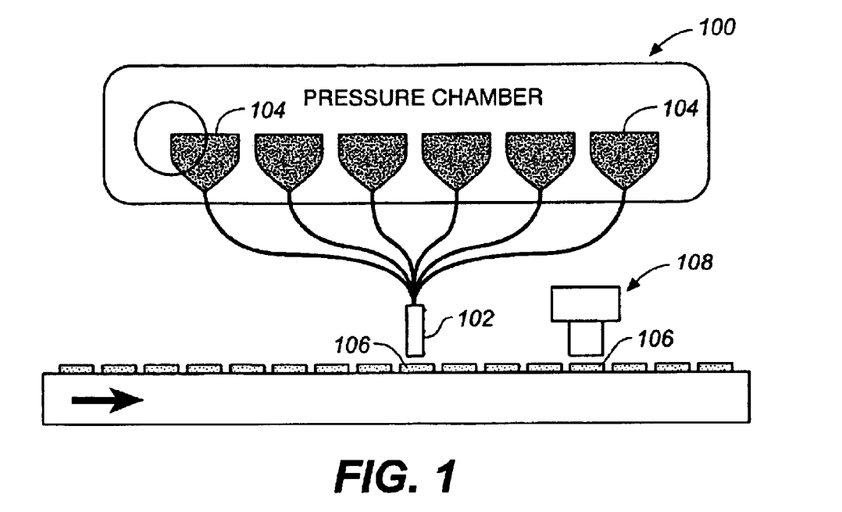
FIG. 1 is a schematic diagram of one embodiment of a microarray fabrication system.

An example of a microarray fabrication system based on this invention is illustrated schematically in FIG. 1. The system 100 may include a print-head 102 that comprises a special unitary capillary bundle 104 or an assembly of capillary bundles from a number of such unitary capillary bundles. Although the unitary capillary bundles are illustrated to be in a pressure chamber, the invention is not limited as such. Each capillary in the bundle may be fluidly linked to a reservoir containing a specific DNA sample. Probes are delivered to the print-head 102 via the unitary capillary bundles 104 and the entire set of probes can be deposited on to the substrate 106 in a single printing action. The invention may include an inspection system 108 to inspect the quality of the fabricated microarrays online or offline.

The basic elements of this invention include methods and apparatus for print-head, fluid delivery, probe deposition and inspection. A discussion of the details of these technological elements follows. Throughout this application, the terms "capillary channel", "channel" or "micro-channel", are used interchangeably and are intended to mean the micro-channel that runs along the unitary capillary bundle from a distal end to a proximal end. The terms "well" or "microwell", are intended to be used interchangeably and to mean the micro-well located at a distal end of the unitary capillary bundle about a micro-channel where it exits the unitary capillary bundle.

1. Print-Head

Figure 2:
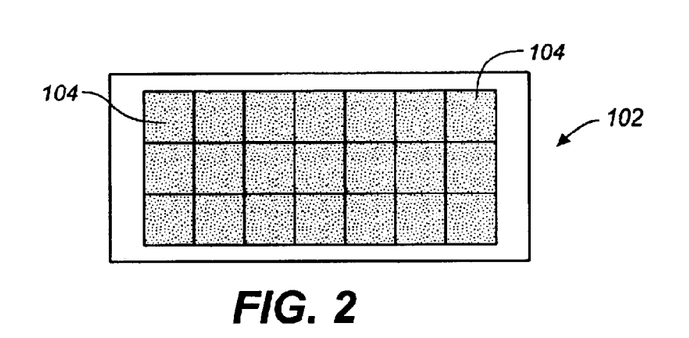
FIG. 2 illustrates a print-head containing the immobilized portion of twenty-one capillary bundles.

The print-head 102 gathers probe fluids from their individual reservoirs and deposits them in small volumes on to the microarray substrate at each printing action. A print-head 102 may be a solidified or otherwise joined piece and its facet is fabricated to conform to the surface contour of the microarray substrate 106 in order to facilitate uniformed probe deposition. The print-head 102 may contain a single or multiple unitary capillary bundles 104. In the variation of the multiple bundle print-head 102 configuration, shown in FIG. 2, the shape of each bundle is rectangular or square allowing for ease of assembly of the capillary bundles 104 to form a structured matrix in a rectangular print-head 102. However, the invention may include any other outline shapes. Although the variation of FIG. 2 illustrates a print-head 102 as having a 3×7 configuration of unitary capillary bundles 104 the invention is not limited as such. The number of unitary capillary bundles 104 may be selected as desired. The rectangular print-head 102 configuration yields several advantages. For example, the rectangular print-head 102: 1) makes the best use of the surface area of a standard microscope slide; 2) permits pre-determination of the position and orientation of each bundle 104 in the system; and 3) allows identification of each capillary in a bundle. The capillaries used in the invention can be made of silica or other suitable materials such as glass, ceramics, polymer or metal.

Unitary Capillary Bundle

Figure 3:
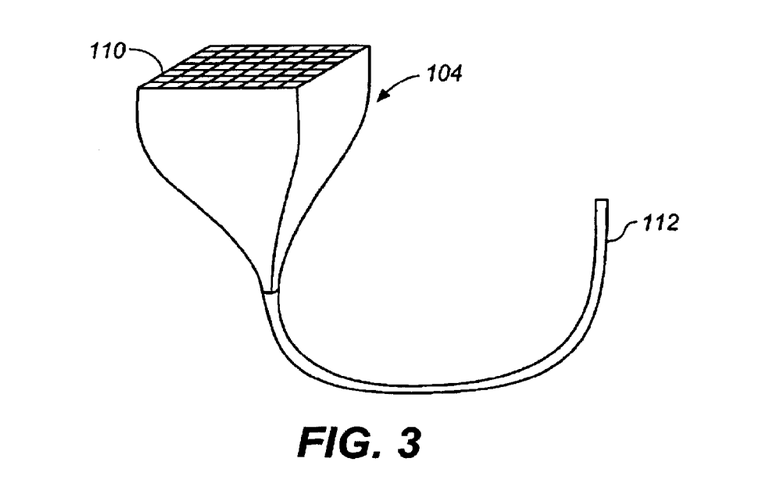
FIG. 3 illustrates an example of a unitary capillary bundle.

As shown in FIG. 3, the unitary capillary bundle 104 in the system is a single continuous structure, particularly when viewed along a cross-section that is orthogonal to its length. For example, the single continuous structure may be fabricated by taking discrete capillary preforms each having a channel extending throughout the preform and joining the preforms together through, for example, a heating process which causes the individual preforms to form into a continuous structure with multiple capillary channels. Therefore, the bundle 104 no longer comprises a number of contiguous preforms that are merely fastened together. Instead, the bundle 104 is now a continuous unitary structure. The unitary capillary bundle 104 may have a proximal end 110, where probe material may be provided, and a distal end 112 which may be joined into a print-head. The capillary bundle 104 should be continuous in at least the proximal 110 and distal ends 112. However, the capillary bundle 104 may also be continuous throughout its entire body. The unitary capillary bundle 104 may be flexible throughout its length, but is flexible at least towards its distal end 112. Such flexibility allows for stationary placement of a separate reservoir for probe material (not shown) or for stationary placement of the proximal end 110 as reservoirs, while the distal end 112 moves as the print-head deposits the probe material. The unitary capillary bundle 104 preferably comprises a large number of fluidly isolated inner channels. However, any number of fluidly isolated inner channels is contemplated to be within the scope of the invention. In one variation of the invention, each channel may be shaped as a funnel with a larger opening at the proximal end 110 (input end) and a smaller opening at the distal end 112 (output end). The channel openings therefore form an orderly matrix at each end of the bundle with different spatial pitches. The use of the term "orderly matrix" means that the position/location of the channel openings corresponds between the ends of the bundle 104. For example, knowing the position of a particular channel on a first end of the bundle 104 enables the determination of the corresponding channel at the second end of the bundle 104 by locating the corresponding position at the second end of the bundle 104.

Along the length of the unitary capillary from proximal 110 to distal 112 end, all dimensions may be uniformly reduced at different cross-sections. As illustrated in FIG. 3, the bundle 104 cross-section may be large at the proximal end 110 and may be sufficiently smaller towards the distal end 112 while being essentially uniform. The large inner volume of each channel at the portion near the proximal end 110 may serve as probe reservoir, while the distal end 112 may be used to deposit the probe onto the microarray substrate. In another variation of the invention, the channel matrix at the proximal end 110 may have the same spatial pattern and pitch as wells in a standard microtiter plate (not shown) to facilitate convenient transfer of probe material from the microtiter plate to the unitary capillary bundle 104. The channel matrix at the distal end 112 determines the pitch and pattern of the probe array on the fabricated microarray.

Such a special capillary bundle can be fabricated from a large preform using extrusion or drawing process as described in many patents including U.S. Pat. Nos. 5,265, 327 and 4,010,019, the entirety of each of which is incorporated by reference herein. A wide range of materials can be used to fabricate the device including, but not limited to glass, ceramic, and polymer.

Figure 4A:
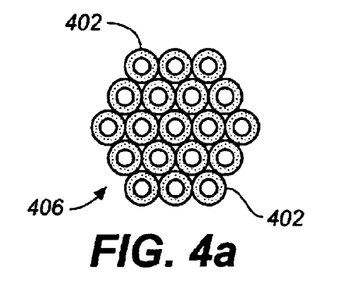
FIGS. 4a–4c illustrates the fabrication of a unitary capillary bundle with orderly arrangement of capillaries.
Figure 4B:
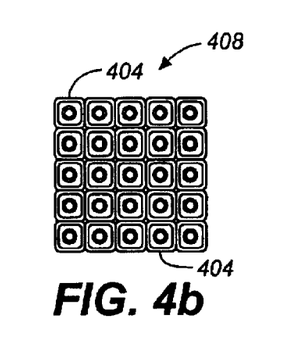
Figure 4C:
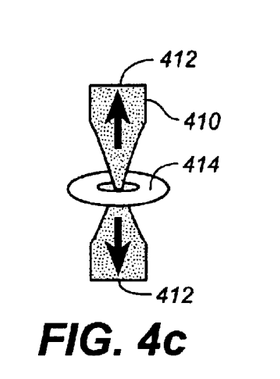

One fabrication method is described as follows and is illustrated in FIGS. 4a–4c. Preforms 402, 404 (e.g., glass tubes) may be selected with outer cross-section size that is equal to the desired intended pitch at a proximal end of a unitary capillary bundle. As shown in FIGS. 4a–4b, the preforms 402, 404 may be stacked into an orderly matrix 406, 408. A matrix may be formed in a honeycomb, chessboard, or other desired pattern depending on the outline shape of the preform and the stacking method used to join the preforms. The orderly matrix 406,408 may then be joined together to form an orderly unitary matrix structure. An example of a joining method includes the use of heat to weld the preforms together. As illustrated in FIG. 4c, the unitary matrix 410 may then be extended, for example, by an extruder or drawn on a fiber draw tower. In this process, each end 412 of the unitary matrix 410 remains unchanged while the middle section is thinned into a flexible capillary bundle having a matrix arrangement of a desired pitch. The unitary matrix is then separated at the middle section and can therefore produce two special unitary bundles, one end 412 of which is a 2D array of rigid and large tubes with sizes compatible to the microtiter plates, while the other end 414 is a 2D array of fine capillaries of the same configuration. The positions of each capillary in the bundle are highly organized and can be registered according their position orders in the bundle. In such a case, the ends 412 of the pre-extended unitary structure become proximal ends of the resulting unitary capillary bundles, while the separated ends 414 become distal ends of the resulting unitary capillary bundles.

As discussed below, the unitary capillary bundle of the present invention may contain additional features to assist in the production of microarrays. The first additional feature is that a unitary capillary bundle of the present invention may be fabricated to transmit light through its core or channel as well as transport a probe sample through its channel or core region. The ability of a unitary capillary bundle to transmit light is very useful for conducting light activated modification or chemical reaction at the surface of a substrate. A second additional feature of the unitary capillary bundle of the present invention is that the bundle may contain a well (also referred to as a "micro-well") at a distal end of the unitary capillary bundle where the channel exits from the bundle. These micro-wells assist in confining probe samples deposited onto the substrate to remain within the well. The confinement of the probe sample to within the well thus prevents overlapping spots or cross-talk between adjacent probes.

In one variation of the invention, a tube preform made of glass may have an inner region around the central cavity that is doped with a rare earth element, such as Germanium, Erbium, etc. Such a preform will have form a core region with a higher optical refractive index than the surround cladding. Such a special preform can be fabricated using a Modified Chemical Vapor Deposition (MCVD) process that is widely used in the fiber optics industry. Alternatively, such a special preform may be made by simply drilling a hole through the center of a normal multimode optical fiber preform. An additional advantage in using such a special tube preform for the unitary bundle fabrication is that the micro-well can be fabricated around the center of each micro-channel on the facet of the print-head by simply dipping the print-head into a etching fluid, e.g., a Fluoride acid.

An example follows of how a unitary capillary bundle may be configured to create an array at a distal end. Assuming that an original tube preforms to have a 3 mm×3 mm square shaped cross-section, a cross-section of a 20×20 array of these original preforms measures as 6 cm×6 cm. After joining the preform stack array into a unitary structure, for example by welding, heating, etc., the stack may be drawn down to 1 mm×1 mm at the distal end, over a length of 1 meter. The unitary bundle, now containing 400 micro-channels, is sufficiently flexible at the distal portion and has a 50 $\mu$m channel pitch at the distal facet. The probe pitch produced by this bundle is 50 $\mu$m. Assembling an array of 20×60 such unitary capillary bundles in an orderly way produces a print-head containing an orderly matrix of almost a half-million micro-channels. Yet, the print-head remains small enough to fit in a standard microscope slide. Because the array is orderly, unlike randomly bundled capillaries, identification of channels at the distal end as they correspond to channels at the proximal end is not required.

This geometry feature of the unitary capillary bundle, being relatively long, flexible and having large portion along its length of a uniformly small cross-section, is very beneficial for microarray fabrication. First, the flexibility and size uniformity towards the distal end permits assembly of a print-head with a large number of unitary capillary bundles comprising much larger number of micro-channels. Second, as mentioned above, the reservoir portion at the proximal end of the bundle may be held stationary during printing, which helps in keeping a stable probe flow towards the print-head. Finally, the relatively long, small inner channel reduces the impact of positive capillary pressure created during direct contact printing, which, as described below, may contribute to probe overflow and overlap on the microarray.

2. Fluid Delivery

The functions of the fluid delivery sub-system in the arrayer include: transporting probe fluid from the reservoir of the unitary capillary bundle to the print-head through the respective channel; and ensuring a constant and uniform flow rate in each channel across the print-head.

Fluid Transport

This invention includes several methods to drive the probe fluid from the reservoir into the channel and towards the print-head. These methods may be used alone or in combination in the fluid delivery sub-system.

The methods include the use of air pressure, gravity, and/or an electric field.

Driving the probe by the use of air pressure includes establishing and maintaining a differential air pressure between the proximal and distal ends of the unitary capillary bundles. This pressure differential translates into hydraulic pressure to drive the probe fluids.

Gravity may be used to drive the probes once the capillaries are filled with the probe fluids. A constant flow can be maintained and controlled by adjusting the vertical positions of the fluid reservoirs, e.g. the microtiter plates, with respect to the position of the print-head.

An electric field may be used in those cases where the probe material can carry an electrical charge. For example, because DNA fluids are negatively charged, a voltage applied between the reservoir and the print-head can be used to control the flow of the fluid through electrostatic and electroosmotic force (EOF). The use of an electric field to drive the probe material is described in "Capillary Electrophoresis, Theory and Practice", by Camilleri, CRC Press, ISBN 084939127X Flow Rate Control Controlling the flow rate such that it is constant in each channel and uniform across the print-head increases the probability that the probe spot sizes on the substrate are constant from array to array and uniform across each microarray.

Holding the fluid flow in a capillary channel to a constant rate is relatively easy. All fluid driving methods described above may be used to control the flow rate. However, air pressure and gravity are relatively imprecise mechanisms for flow rate control. When air pressure or elevation differences disappear, because of back-pressure which builds in the capillary channel, the flow does not stop instantly. In comparison, an electric field provides a much more precise and responsive mechanism for controlling probe flow.

It is much more difficult to ensure the uniformity of flow rates in every capillary channel of the print-head. Flow rate in a capillary channel is dependent upon many factors besides the driving force. Such factors include cavity size, the surface characteristic of the capillary, and fluid viscosity. Clogging and bubble entrapment in capillaries may also impede uniformity of probe flow resulting in missing probes on the fabricated microarray. Thus, it is desirable to minimize factors that prevent uniform probe flow.

Another aspect of this invention provides measures to ensure the flow rate uniformity. Variations of the invention include enhancing the uniformity of flow rate by selecting a silica based capillaries, altering probe fluid viscosities, preventing clogging of the capillary channels, preventing bubble formation and entrapment within the channels, and using an individual electric field to control flow rate.

The first variation of the invention which ensures uniform flow rate is the use of silica based capillaries. The characteristics of silica capillaries are suited towards the manufacture of micro-arrays. Both inner and outer diameters of silica capillaries can vary less than 2% in a same draw and less than 5% between different draws. Therefore, it is desirable to use only capillaries made of the same draw to enhance the dimensional uniformity between the capillary channels in the unitary capillary bundle. Also, the surface of the silica capillary is smooth after the drawing process because the drawing of the capillaries is carried out at melting point of the silica. In addition, the silica surface in the capillary is naturally negatively charged, which makes it "phobic" to DNA samples, resulting in minimum friction between sample and capillaries. The natural charge of the silica surface in the capillary channel ensures smooth delivery of sample fluids to the print-head. Moreover, the channel walls may also be coated with other hydrophobic films such as fluorocarbon polymer to further enhance the durability and uniformity of the capillaries.

Another variation of the invention includes ensuring flow uniformity by altering the viscosity of the probe fluids. For example, the viscosity of probe fluids may be adjusted by adding a suitable amount of inert buffering material, such as sugar, to probe fluids.

Another variation of the invention which increases the uniformity of flow is prevention of clogging of capillary channels and prevention of the formation of bubbles within the probe fluid. For example, all probe fluids can be purified and handled in clean room environment to prevent capillary clogging. Bubble entrapment can be eliminated by preprocessing fluids with ultrasound and vacuum suction.

Figure 5:
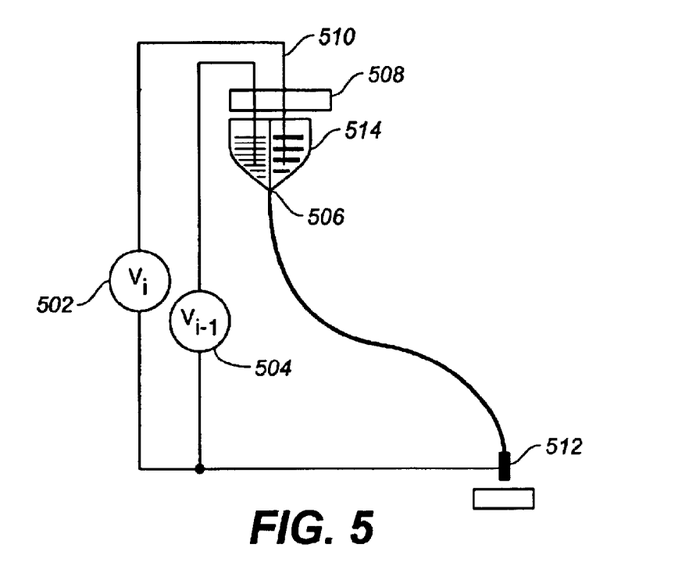
FIG. 5 illustrates two methods of controlling flow rate of probe-containing solution through capillaries, i.e. the use of pressurized gas, and the use of voltage.

Control flow rate in each capillary is also accomplished with the use of individual electric fields. Using the first three measures described above, it is highly probable that the flow rate variation across the print-head can be kept within a small range (e.g. 20%) under a uniform driving force such as air pressure or gravity. These methods are sufficient for production of most microarrays. In cases where more precise flow control is required, an electric field method can be used to control the flow rate in each individual capillary channel. FIG. 5 illustrates an embodiment of a flow control sub-system where gravity and/or air pressure are used as the primary fluid driving force and an electric field 502, 504 is used as an additional, fine adjustment mechanism for flow control. As illustrated, different voltages may be applied to the different reservoirs or channels of the unitary capillary bundle 506. For example, electrodes may be held in contact with each channel by the use of an electrode frame 508 which suspends an electrode 510 directly into a channel of the unitary capillary bundle. Also, the end-facet of the print-head 512 and each capillary tip at a proximal end may be coated with a conductive material, e.g., metal. All capillaries at the print-head 512 may be held at a common ground. Different voltages may be applied to the different capillary tips at the proximal end 514. The resulting electric field fine-tunes the flow rate in the capillary. Because the electrical field is used only as a fine-tuning device instead of the primary means to propel the fluid, a relatively small voltage may be sufficient. Moreover, voltages may be adjusted based on feedback from inspection devices, as discussed below, or by monitoring the size of the deposited droplets of probe-material using e.g., an optical or scanning microscope.

3. Probe Deposition

The probe deposition sub-system, as discussed above, ensures that a uniform volume of probe fluid is deposited onto the substrate and that there are no missing or overlapped spots on the microarray. This invention further includes mechanical tapping and electrostatic printing as deposition mechanisms.

Mechanical Tapping

Figure 6A:
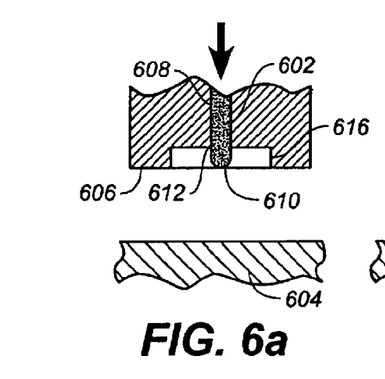
FIGS. 6a–6c illustrate probe deposition by mechanical tapping. In these illustrations, the channel of the print-head is illustrated with a well.
Figure 6B:
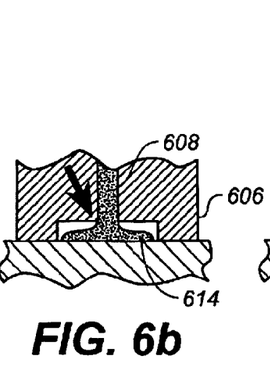
Figure 6C:
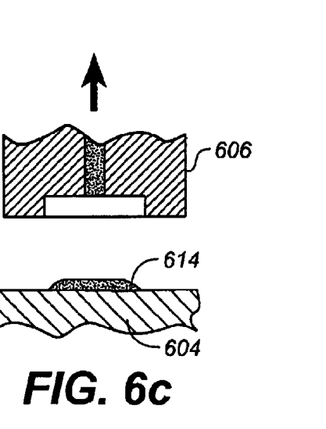

As illustrated in FIG. 6, probes 602 can be deposited on to the microarray substrate 604 by mechanically tapping the print-head 606 on the substrate 604. As shown in FIG. 6a, the constant flow of probe solutions 602 in the capillary channel 608 produces a micro sphere 610 of probe fluid 602 at the facet 612 of each capillary channel 608. When the print-head 606 is tapped on the substrate 604, the droplet 610 bonds to the substrate 604 due to surface tension as shown in FIG. 6b. This surface tension overcomes the binding force in the fluid 602. The droplet 610 thus breaks away from the fluid column at its weakest point, i.e. exiting point of the capillary channel 608, when the print-head withdraws as shown in FIG. 6c. A probe spot 614 is deposited on the substrate.

The invention described herein avoids two problems commonly associated with microarrays, namely missing and overlapping probe spots in the microarray. This invention provides the measures, which can be used alone or in combination, to prevent missing spots on the fabricated microarray.

1) In one variation, the surface of the print-head facet should be in contact with the substrate essentially across its entire face during a tap action. When a microscope slide is used as the microarray substrate, the surface of the print-head facet should be polished to a high degree of flatness.

Figure 7A:
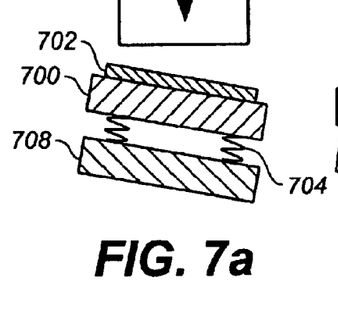
FIGS. 7a–7c illustrate an example of a spring-mounted substrate holder that provides improved alignment between substrate and print-head
Figure 7B:
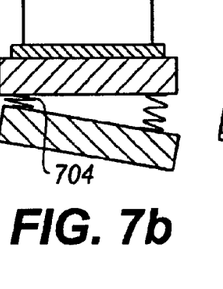
Figure 7C:
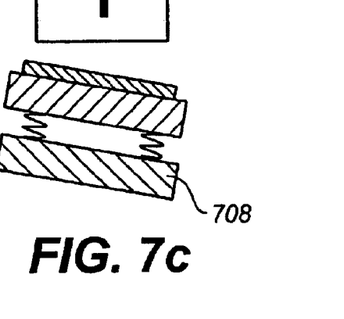

2) In another variation, one of the contacting parts, i.e. print-head or the substrate, could be rigidly supported while the other is fixed on a soft or spring-loaded platform. If these two surfaces are slightly unparallel, the one on the soft support will yield to the one on the rigid mounting to ensure perfect contact. For example, as illustrated in FIGS. 7a–7c, a platform 700 containing a substrate 702 may be spring loaded 704 to a fixed base 708. Or, for example, the platform 700 may be mounted on joints or gimbals, or may be a polymeric or sponge-like block on which the substrate rests. Therefore, as the print-head 706 approaches the substrate, the pliant nature of the mount 700 will correct any misalignment between the mount 700 and the print-head 706. Although not illustrated, the print-head may be placed on a pliant mount, or the print-head may comprise a pliant material which accounts for any misalignment between a print-head and a substrate. Also, if the configuration of the print-head and substrate is such that the print-head never contacts the substrate, contact may be made between, for example, a frame of the print-head and a support of the substrate, to ensure that the print-head and substrate are parallel to each other during deposition of the probes.

3) In another variation of the invention, the substrate surface can be treated to become positively charged while the print-head facet is made to be negatively charged and hydrophobic.

Overlapping spots (also referred to as probe "cross-talk" or "cross-communication") may be caused by excess amount of probe fluid deposited on the substrate combined with a lack of means to confine the deposited fluid within a certain area on the substrate. Although, flow rate controls described above help to prevent fluid overflow, capillary forces may be created between the print-head facet and the substrate when the print-head is brought very close to the substrate and a fluid link is established between the two surfaces. These capillary forces may pull extra fluid out of the channel. The invention described herein further provides the following aspects, which can be used alone or in combination, to prevent overlapping spots on the fabricated microarray:

1) Making both the print-head and substrate surfaces hydrophobic.

2) Using wells or microwells as illustrated in FIGS. 6a–6c. A micro well 616 or well 616 may be fabricated at the tip of each capillary channel 608. This micro well can accommodate the volume of fluid 602 placed on the substrate 604. Micro wells can be produced, for example, either one-by-one using a diamond tipped precision drill or in parallel using photolithographic methods. If the capillary has a central region doped with Germanium (originally designed for light transmission as described above), these micro wells can be fabricated in parallel by dipping the print-head into an etching fluid, such as fluoride acid solution such as HF, because a very small Ge doping can dramatically accelerate the etching rate of the silica in the vicinity of the Ge. The micro well 616 assists in controlling the size of probe material 602 that is deposited on the substrate 604. The micro wells 616 may provide a physical barrier to the probe material 602 only allowing deposition of the probe material 602 within the well 616. Retaining probe material 602 within each respective micro well 616 prevents cross-talk of adjacent probe materials. The shape or cross section of the micro wells 616 is not limited to the figures and may be selected as desired.

3) Increase the viscosity of the deposited probe materials by increasing the sample density in its solution or by adding sufficient amount of inert buffering materials. Print probes in bead, gel or paste forms can eliminate overlapping problems.

4) Reduce the time in which the print-head is in fluid contact with the substrate.

5) Use capillaries with a smaller inner diameter, which will reduce the effect of the capillary pulling force generated in the fluid layer between the print-head and the substrate during contact printing.

6) Deposit probes on hot substrates in a dry environment, which accelerates the evaporation of fluids in the probe and reduces overflow.

7) Deposit probes on a substrate that has a surface temperature below the freezing point of the probe fluid.

Electrostatic Printing

Figure 8:
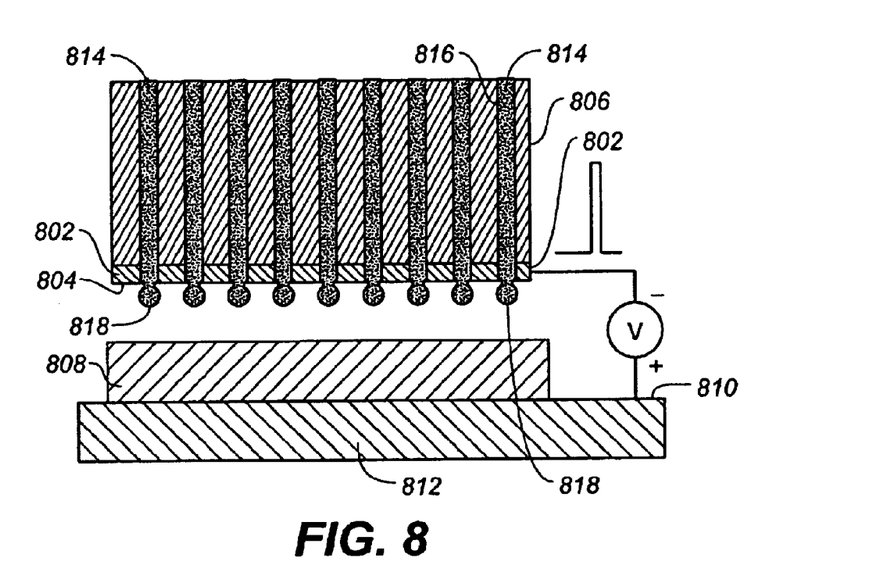
FIG. 8 illustrates an example of a method of depositing probes by electrostatic printing.

As shown in FIG. 8, a conductive layer 802, such as metal, can be coated on the facet 804 of the print-head 806 and the microarray substrate 808 is placed on a conductor 810 or conductor coated support 812. Alternatively, a special microarray substrate 808 with a conductive layer can be used. When a voltage (V) is applied between the print-head 806 and the substrate 808 or its support 812 with positive polarity at the substrate end, the probe material 814, e.g., DNA samples, in the capillary channels 816 will be attracted towards the substrate 812 because of their negative charges. If a short pulse of sufficiently high voltage is applied when the print-head facet 804 is close to the substrate, spots 818 of the various probe fluids are torn from the capillary channels 816 and are propelled to the substrate 808. One advantage of this method is that the print-head 806 does not have to touch the substrate surface 808, thus eliminating many potential problems associated with missing or overlapping spots on the fabricated microarray. In addition, the print-head may be stationary, thus eliminating the need for a micro well at the end of the capillary channel.

Printing Beads, Gel, Paste

Another variation of the invention that avoids probe cross-talk is by printing probes on carriers which take the physical forms of microspheres (beads), gels or pastes. In particular, using beads as a carrier has additional advantages. For example, many synthesized biomolecules, such as oligonucleotides, are produced on beads. Thus, printing beads eliminates the need to cleave the molecule from the beads. Also, beads reflect incident light several times within the bead or among adjacent beads before bouncing the light back. This increases the efficiency of fluorescent excitation thus improves the signal to noise ratio during microarray readout.

Figure 9:
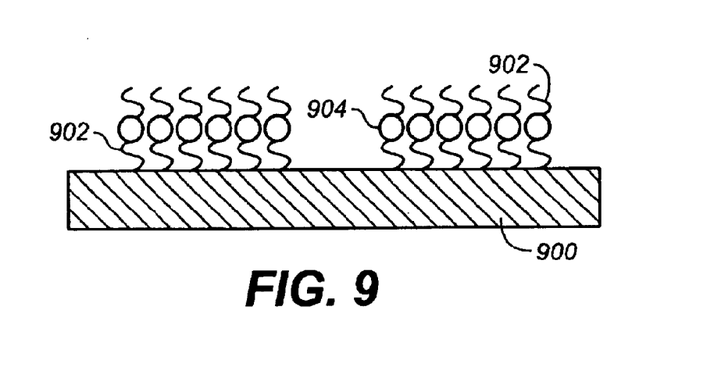
FIG. 9 illustrates a bead array immobilized by probe molecules.

Another variation of the invention includes an array of gel or paste drops deposited at specific locations on the substrate. Each drop may carry a specific probe material. This invention also includes the use of a special bead array, in which beads are not covalently attached to the substrate directly. Instead, as illustrated in FIG. 9, the probe molecules 902 are covalently attached to the beads 904 through function groups at one end of the molecular chain. Upon deposition on the substrate 900, the probe molecules 902 covalently attach to the substrate 900 through proper functional groups at the other end of the molecular chain.

4. Array Inspection

In another aspect of the invention, an array inspection sub-system may be used to monitor the quality of fabricated microarrays. The inspection can be carried out off line or online and in real time. Arrays with missing and overlapped spots are automatically detected, registered and eventually rejected as defect products. The device may also be used to monitor the spot sizes in real time and feed the information back to the fluid delivery sub-system to control the flow rate in the capillary channels. If the spot sizes on the microarray or print-head are uniformly too large or small, the system may be configured to adjust the printing rate accordingly to compensate for a desired change to the spot size by, e.g., adjusting the voltage applied to the individual capillary channels.

This invention offers two different optical designs for the inspection subsystem.

Figure 10:
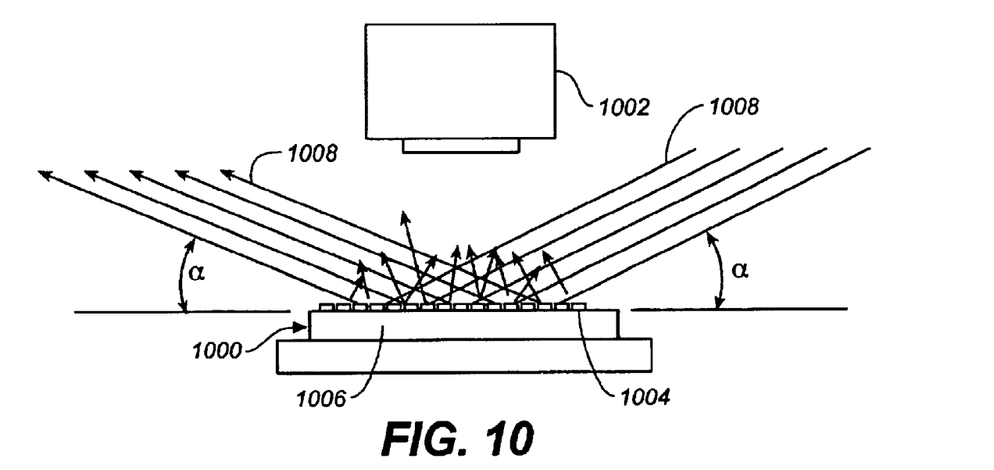
FIG. 10 illustrates equipment for and a method for inspecting a microarray using light-scattering.

The first design, shown in FIG. 10, is based on the detection of light scattered by the spots on the microarray. A fabricated microarray 1000 is illuminated with light projected at a large angle α. A digital camera 1002 observes the microarray 1000 from above. Due to their small fluid volume, probes 1004 deposited on the substrate 1006 will dry almost instantly and deposit a high salt content in the probe fluid solution. The salt in the dried probe 1004 is present in a sufficient amount to scatter light 1008 that shines upon it. At areas on the substrate 1006 where there are no probe spots 1004, there is no salt to scatter the light 1008 and therefore the light 1008 is reflected at the same large angle to the side. Because no light 1008 is reflected towards the camera 1002, the camera 1002 registers a dark background in these areas. At areas where there is a probe deposit 1004, the salt scatters the light 1008 towards the camera 1002, and the camera 1002 registers bright spots in the areas where probes 1004 are deposited.

Figure 11A:
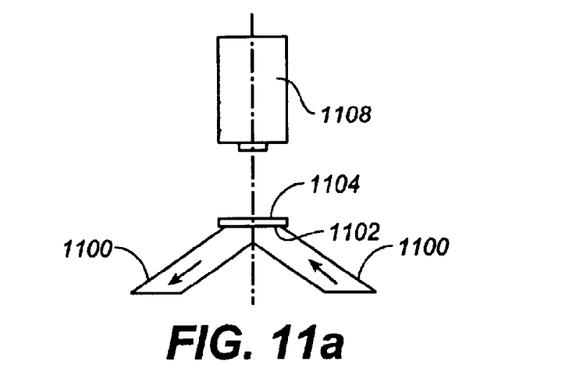
FIGS. 11a–11c illustrate equipment for and a method for inspecting a microarray using total internal reflection of light within the substrate.
Figure 11B:
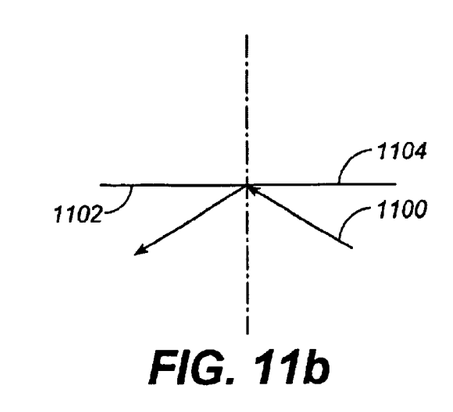
Figure 11C:
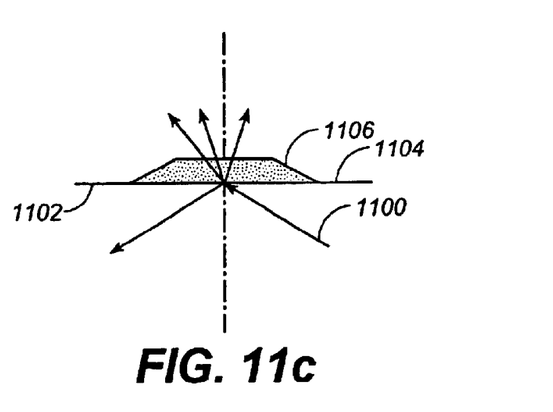

An alternate design, shown in FIGS. 11a–11c, is based on the principle of total internal reflection and is suitable for the inspection of microarrays which may not be well suited for examination by the previously discussed method. In this variation, a collimated light beam 1100 is projected to the bottom surface 1102 of the slide 1104 on which the probe array is deposited. The angle of incidence of light 1100 to the bottom surface 1102 is slightly larger than the critical angle of total internal reflection at the substrate-to-air interface. FIGS. 11b–11c illustrate magnified views of the substrate 1104 with the light beam 1100 projected on the bottom surface 1102 of the slide 1104. A digital imaging camera 1108 is used to observe the illuminated region above the substrate surface. As illustrated in FIG. 11b, in an area of the substrate 1104 where there is no probe, total internal reflection occurs and little light can be detected by the camera pixel aimed at this location. As illustrated in FIG. 11c, in the area where there is a probe 1106, however, the presence of the probe 1106 destroys the condition of total internal reflection at the substrate-air interface. Part of the light beam will be refracted into the space above the substrate surface and captured by the imager. This method can significantly increase the contrast of most transparent objects.

In either design, multiple cameras may be required at different positions along the microarray carrying stage to cover the entire microarray.

5. Other Potential Benefits of Light Guiding Capillaries

As described above, it is an aspect of this invention that each capillary channel function as an optical waveguide capable of transmitting light. Such a feature may have important utilities for use in microarray fabrication. For example, an array substrate may be coated with a layer of light sensitive material, e.g., a material that is hydrophobic without light exposure and becomes hydrophilic after exposure. Examples of this material include O-carboxymethylated calyx resorcinaren, or other compounds containing photochromic azobenzenes. The inventive capillary channel allows transmission of a light pulse at the very moment that the print-head deposits the probe array onto the substrate. In the case where the light sensitive material serves to make the substrate hydrophilic, the exposure of the light causes a region immediately under the micro-fluid well at each capillary tip to become hydrophilic while leaving the rest of the substrate surface hydrophobic. In this way, not only is a probe confined to a well-defined area, but target sample fluid will also concentrate in the probe region during hybridization stage. In the case where a micro well is used, the light could be confined to the area within the well further defining the target area of the probe. Such a feature improves hybridization efficiency and reduces the required amount of target fluid. Another aspect of the invention is to select a substrate coating material receptive to a particular wavelength of light, so that the substrate-probe cross-linking happens instantly when the probe is laid down in fluid phase. Yet another feature is to incorporate photon cleavable linkers in the probe samples and alter the molecular structures of certain probes or to prevent the fragment from entanglement when they are being laid. It is also possible to activate certain chemical reactions within the probe by illuminating the probe arrays at certain conditions.

6. Additional Applications of the Disclosed Invention

Microtiter plates are the most widely used device for the storage, transport and handling of chemical or biological samples or used as reaction vessel to perform multiple chemical or biological reactions in parallel. In addition to the application of microarray fabrication described above, the disclosed invention can be adapted to transport biological and chemical samples from one or multiple microtiter plates to other locations in a laboratory test system. In particular, it is ideally suited to transfer samples between a standard microtiter plate to other multi-well or multi-channel devices or between standard microtiter plates with the same or different formats (for example from 96-well plate to 364-well plate and vise versa).

What is claimed is:

1. A capillary bundle comprising:
   a body having a proximal end and a distal end;
   a plurality of isolated channels, each of said channels extending from said proximal end to said distal end and being surrounded by a channel wall having a first region in communication with said channel and at least a second region on a side of said first region opposite to said channel, wherein said first region has an optical refractive index higher than an optical refractive index of said second region so that light transmitted into the proximal end of said channel exits the capillary bundle at said distal end of said channel; and
   wherein at least at said proximal and said distal ends, a cross-section of said capillary bundle as defined by any section orthogonal to a length of said capillary bundle comprises a continuous structure.

2. The capillary bundle of claim 1, wherein at least a portion of said body located between said distal end and said proximal end is flexible such that said distal end may move independently of said proximal end.

3. The capillary bundle of claim 1, wherein said first region of said channel wall is doped with Germanium or lead.

4. The capillary bundle of claim 1, wherein at least one of said plurality of channels comprises an individual well located on said distal end where said channel exits from said distal end.

5. The capillary bundle of any of claim 1, 2, 3, or 4, wherein said capillary bundle comprises a continuous cross section throughout an entirety of said capillary bundle.

6. A print system for printing probe microarrays comprising:
   a capillary bundle comprising:
      a body having a proximal end and a distal end;
      a plurality of isolated channels, each of said channels extending from said proximal end to said distal end and being surrounded by a channel wall;
      at least a portion of said body located between said distal end and said proximal end being flexible such that said distal end may move independently of said proximal end; and
   wherein at least at said proximal and said distal ends a cross-section of said capillary bundle as defined by any section orthogonal to a length of said capillary bundle comprises a continuous structure;
   a plurality of reservoirs in fluid communication with said proximal ends of said channels of said capillary bundle;
   a voltage source connected to an electrically-conductive material at said proximal end and an electrically conductive material at said distal end of each of said channels; and
   a voltage controller being configured to individually adjust and control the voltage applied to each of said channels.

7. A print system for printing probe microarrays comprising:
   a capillary bundle comprising:
      a body having a proximal end and a distal end;
      a plurality of isolated channels, each of said channels extending from said proximal end to said distal end and being surrounded by a channel wall having a first region in communication with said channel and at least a second region on a side of said first region opposite to said channel, wherein said first region has an optical refractive index higher than an optical refractive index of said second region so that light transmitted into the proximal end of said channel exits the capillary bundle at said distal end of said channel; and
      wherein at least at said proximal and said distal ends, a cross-section of said capillary bundle as defined by any section orthogonal to a length of said capillary bundle comprises a continuous structure; and
   a plurality of reservoirs in fluid communication with said proximal ends of said channels of said capillary bundle.

8. A print system according to claim 6, further comprising a second plurality of reservoirs in fluid communication with said channels at said distal ends of said capillary bundle.

9. The print system of claim 6 or 7, wherein at least a portion of said channel wall is coated with a hydrophobic film.

10. The print system of claim 6 or 7, wherein said plurality of channels form a first arrangement at said proximal end, and a second arrangement at said distal end, and wherein said first arrangement is identical to said second arrangement.

11. The print system of claim 6 or 7, wherein a cross-sectional area of each of said channels in said first arrangement is greater than a cross-sectional area of each of said channels in said second arrangement.

12. The print system of claim 6 or 7, wherein said distal end of said capillary bundle contains at least 10,000 channels that print non-overlapping spots in an area of no more than 12 $cm^2$ on a substrate.

13. The print system of claim 6 or 7, wherein said distal end of said capillary bundle contains at least 100,000 channels that print non-overlapping spots in an area of no more than 12 cm² on a substrate.

14. A print system according to claim 6, 8, or 7, wherein said plurality of reservoirs comprises a microtiter plate having wells.

15. A print system according to claim 6, 8, or 7, wherein said channels at said distal end have an increased cross sectional area such that said distal end channels serve as reservoirs.

16. A print system according to claim 6, 8, or 7, and further comprising a flexible mount on which a substrate is placed prior to printing, said flexible mount being configured to move so that said capillary bundle for printing probe arrays contacts said substrate across said distal end of said capillary bundle despite said print-head and said substrate being aligned so that said print-head would not contact said substrate across said distal end of said capillary bundle in the absence of said flexible mount.

17. A print system according to claim 6, 8, or 7, wherein said plurality of reservoirs reside in fixed positions, and wherein said capillary bundle for printing probe arrays is movable in relation to said reservoirs.

18. A print system according to claim 6, 8, or 7, further comprising a probe selected from a group consisting of deoxyribonucleic acids (DNA), ribonucleic acids (RNA), synthetic oligonucleotides, antibodies, proteins, peptides, lectins, modified polysaecharides, synthetic composite macromolecules, functionalized nanostructures, synthetic polymers, modified/blocked nucleotides/nucleosides, modified/blocked amino acids, fluorophores, chromophores, ligands, chelates, haptens and drug compounds.

19. A print system according to claim 8, wherein said second plurality of reservoirs comprises a microtiter plate having wells.

20. A print system according to claim 7, wherein at least a portion of said body located between said distal end and said proximal end is flexible such that said distal end may move independently of said proximal end.

21. A print system according to claim 6 or 7, wherein at least one of said channels has an individual well where said channel exits said capillary bundle from said distal end.

22. A print system according to claim 6 or 7, wherein said capillary bundle comprises a continuous cross section throughout an entirety of said capillary bundle.

23. A capillary bundle according to claim 1, wherein at least one of said channels has an individual well where said channel exits said capillary bundle from said distal end.

* * * * *